United States Patent
Ohuchi et al.

(10) Patent No.: US 9,855,024 B2
(45) Date of Patent: Jan. 2, 2018

(54) MEDICAL DIAGNOSTIC IMAGING APPARATUS, MEDICAL IMAGE PROCESSING APPARATUS, AND CONTROL METHOD FOR PROCESSING MOTION INFORMATION

(71) Applicant: TOSHIBA MEDICAL SYSTEMS CORPORATION, Otawara-Shi (JP)

(72) Inventors: Hiroyuki Ohuchi, Otawara (JP); Yasuhiko Abe, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 51 days.

(21) Appl. No.: 14/824,624

(22) Filed: Aug. 12, 2015

(65) Prior Publication Data

US 2015/0342571 A1  Dec. 3, 2015

Related U.S. Application Data

(63) Continuation of application No. PCT/JP2014/055825, filed on Mar. 6, 2014.

(30) Foreign Application Priority Data

Mar. 6, 2013 (JP) ................................. 2013-044777

(51) Int. Cl.
  *A61B 8/08* (2006.01)
  *G06T 7/00* (2017.01)
  (Continued)

(52) U.S. Cl.
  CPC .......... *A61B 8/5284* (2013.01); *A61B 8/0883* (2013.01); *A61B 8/461* (2013.01);
  (Continued)

(58) Field of Classification Search
  CPC ... A61B 8/0883; A61B 8/5284; A61B 8/5292; A61B 8/461; A61B 8/463; G06T 7/0012;
  (Continued)

(56) References Cited

U.S. PATENT DOCUMENTS 8,165,371 B2 * 4/2012 Bi ...................... G01R 33/5635
                                                            382/128
9,060,686 B2 * 6/2015 Abe .................... A61B 5/0048
  (Continued)

FOREIGN PATENT DOCUMENTS

JP    2006-026151 A    2/2006
JP    2007-202957 A    8/2007
  (Continued)

OTHER PUBLICATIONS

International Search Report dated Apr. 8, 2014 for PCT/JP2014/055825 filed on Mar. 6, 2014 with English Translation.
  (Continued)

*Primary Examiner* — Sean Conner
*Assistant Examiner* — Pinalben Patel
(74) *Attorney, Agent, or Firm* — Oblon, McClelland, Maier & Neustadt, L.L.P.

(57) ABSTRACT

A medical diagnostic imaging apparatus includes identification-information-changing circuitry and comparison-result-calculating circuitry. The identification-information-changing circuitry changes identification information given to a plurality of points corresponding to contours of tissue in first medical-image-data in a first medical-image-data group each including a plurality of pieces of medical-image-data of different time phases. The comparison-result-calculating circuitry associates the identification information on the points in the first medical-image-data after a change and identification information given to a plurality of points corresponding to the contours of tissue in second medical-image-data
  (Continued)

corresponding to the time phase of the first medical-image-data out of a second medical-image-data group each including a plurality of pieces of medical-image-data of different time phases, compares pieces of motion information representing motion of the tissue in the respective pieces of medical-image-data in the first and the second medical-image-data groups between corresponding time phases based on the association, and calculates a comparison result.

11 Claims, 11 Drawing Sheets

(51) Int. Cl.
G06T 7/20 (2017.01)
A61B 8/00 (2006.01)
G06T 7/215 (2017.01)

(52) U.S. Cl.
CPC ............ *A61B 8/463* (2013.01); *A61B 8/5292* (2013.01); *G06T 7/0012* (2013.01); *G06T 7/215* (2017.01); *G06T 2207/10016* (2013.01); *G06T 2207/10136* (2013.01); *G06T 2207/30048* (2013.01); *G06T 2210/41* (2013.01)

(58) Field of Classification Search
CPC . G06T 2207/10016; G06T 2207/10136; G06T 2207/30048; G06T 2210/41; G06T 7/2006
See application file for complete search history.

(56) References Cited

U.S. PATENT DOCUMENTS

| 9,078,567 | B2* | 7/2015 | Fuimaono | A61B 5/055 |
| 2002/0102023 | A1* | 8/2002 | Yamauchi | G06F 19/3437 382/199 |
| 2006/0170714 | A1* | 8/2006 | Kanda | A61B 8/06 346/2 |
| 2009/0112088 | A1* | 4/2009 | Ohuchi | A61B 6/5282 600/438 |
| 2010/0074475 | A1* | 3/2010 | Chouno | A61B 5/055 382/107 |
| 2011/0190633 | A1 | 8/2011 | Kawagishi et al. | |
| 2013/0253319 | A1* | 9/2013 | Hamilton | A61B 8/5223 600/438 |
| 2016/0196645 | A1* | 7/2016 | Ohayon | A61B 8/0891 382/131 |

FOREIGN PATENT DOCUMENTS

| JP | 2009-106548 A | 5/2009 |
| JP | 2011-104432 A | 6/2011 |
| JP | 2011-177494 A | 9/2011 |
| JP | 2012-055765 A | 3/2012 |

OTHER PUBLICATIONS

Written Opinion dated Apr. 8, 2014 for PCT/JP2014/055825 filed on Mar. 6, 2014.

* cited by examiner

BEFORE STRESS LOADING

AFTER STRESS LOADING

MEDICAL DIAGNOSTIC IMAGING APPARATUS, MEDICAL IMAGE PROCESSING APPARATUS, AND CONTROL METHOD FOR PROCESSING MOTION INFORMATION

CROSS-REFERENCE TO RELATED APPLICATIONS

This application is a continuation of PCT international application Ser. No. PCT/JP2014/055825 filed on Mar. 6, 2014 which designates the United States, incorporated herein by reference, and which claims the benefit of priority from Japanese Patent Application No. 2013-044777, filed on Mar. 6, 2013, the entire contents of which are incorporated herein by reference.

FIELD

Embodiments described herein relate generally to a medical diagnostic imaging apparatus, a medical image processing apparatus, and a control method.

BACKGROUND

Conventionally, as one method to diagnose a cardiac function using an ultrasonic diagnostic apparatus, a diagnostic method referred to as a stress echo method has been performed. The stress echo method is a diagnostic method to evaluate the motor function of myocardium by exerting a stress load such as an exercise load and a drug load on a subject and using ultrasonic image data collected before and after stress loading.

To evaluate the cardiac function objectively and quantitatively, available is a technology to obtain motion information on tissue of the heart such as displacement and strain. This technology is to estimate the movement of the heart by collecting ultrasonic image data of the heart in time series, performing pattern matching of a local region on ultrasonic images, and tracking the local region. Furthermore, the evaluation of the motor function of the heart is also performed by collecting and comparing pieces of the motion information on the heart before and after stress loading.

DETAILED DESCRIPTION

A medical diagnostic imaging apparatus includes identification-information-changing circuitry and comparison-result-calculating circuitry. The identification-information-changing circuitry changes identification information given to a plurality of points corresponding to contours of tissue in first medical-image-data in a first medical-image-data group each including a plurality of pieces of medical-image-data of different time phases. The comparison-result-calculating circuitry associates the identification information on the points in the first medical-image-data after a change and identification information given to a plurality of points corresponding to the contours of tissue in second medical-image-data corresponding to the time phase of the first medical-image-data out of a second medical-image-data group each including a plurality of pieces of medical-image-data of different time phases, compares pieces of motion information representing motion of the tissue in the respective pieces of medical-image-data in the first and the second medical-image-data groups between corresponding time phases based on the association, and calculates a comparison result.

With reference to the accompanying drawings, the following describes a medical diagnostic imaging apparatus, a medical image processing apparatus, and a control method according to exemplary embodiments.

First Embodiment

Figure 1:
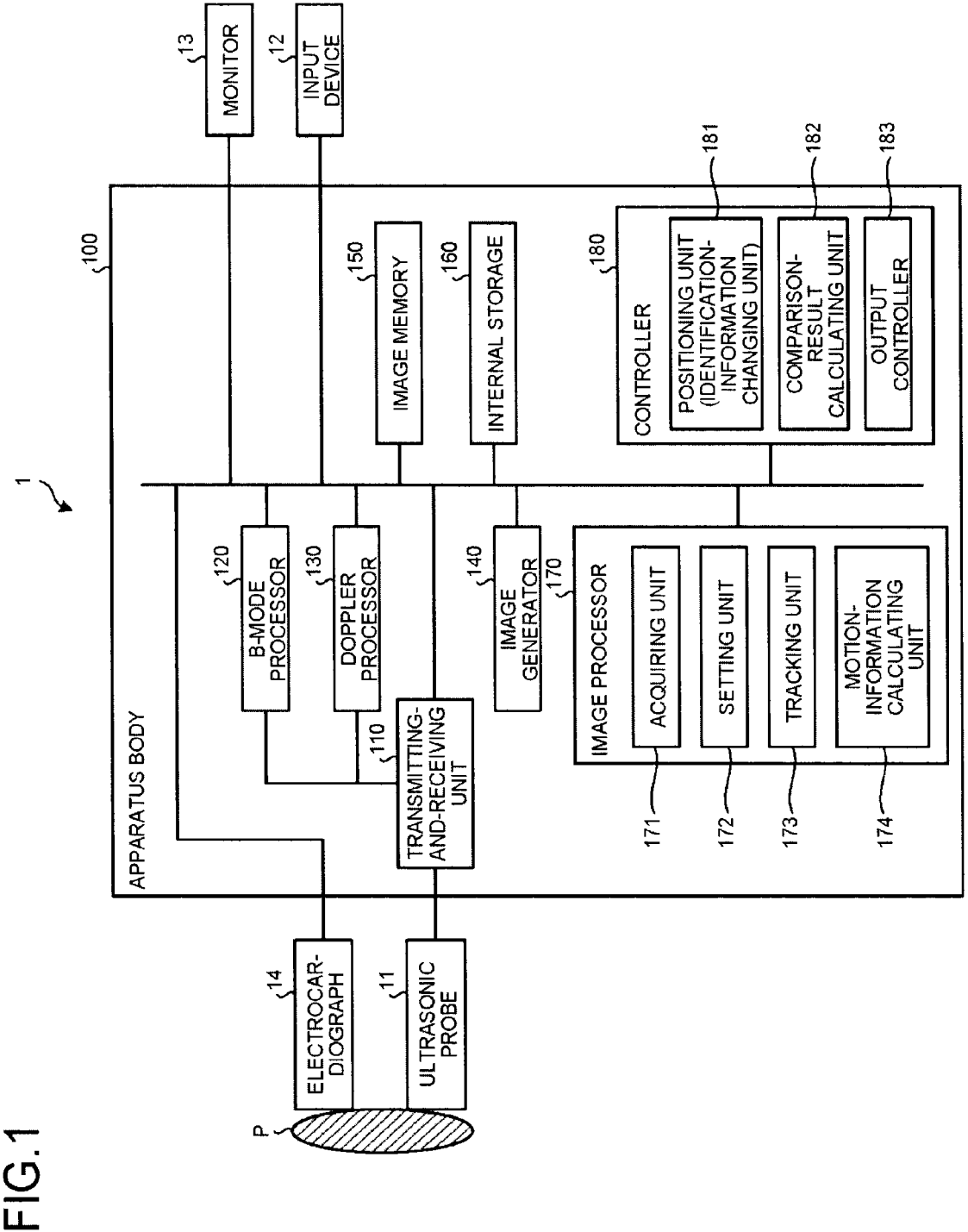
FIG. 1 is a block diagram illustrating an example of the configuration of an ultrasonic diagnostic apparatus according to a first embodiment.

FIG. 1 is a block diagram illustrating an example of the configuration of an ultrasonic diagnostic apparatus according to a first embodiment. As illustrated in FIG. 1, an ultrasonic diagnostic apparatus 1 in the first embodiment includes an ultrasonic probe 11, an input device 12, a monitor 13, an electrocardiograph 14, and an apparatus body 100.

The ultrasonic probe 11 includes a plurality of piezoelectric transducer elements, and these piezoelectric transducer elements generate ultrasonic waves based on a drive signal supplied from a later described transmitting-and-receiving unit 110 of the apparatus body 100. The ultrasonic probe 11 receives reflected waves from a subject P and converts them into an electrical signal. The ultrasonic probe 11 further includes a matching layer that is provided on the piezoelectric transducer elements, a backing material that prevents ultrasonic waves from propagating toward the rear from the piezoelectric transducer elements, and others. The ultrasonic probe 11 is detachably connected to the apparatus body 100.

Upon transmitting ultrasonic waves to the subject P from the ultrasonic probe 11, the transmitted ultrasonic waves are reflected by discontinuous planes in acoustic impedance in the body tissue of the subject P in sequence, and are received by the piezoelectric transducer elements of the ultrasonic probe 11 as a reflected wave signal. The amplitude of the reflected wave signal received is dependent on the difference in acoustic impedance at the discontinuous plane by which the ultrasonic waves are reflected. The reflected wave signal, when transmitted ultrasonic pulses are reflected by the surfaces of blood flow and the heart wall and the like in motion, undergoes frequency deviation that is dependent on the velocity component of a moving body with respect to the transmitting direction of the ultrasonic waves by the Doppler effect.

For example, in the first embodiment, for the two-dimensional scanning of the subject P, a 1D array probe in which a plurality of piezoelectric transducer elements are disposed in a single row is connected to the apparatus body 100 as the ultrasonic probe 11. The 1D array probe as the ultrasonic probe 11 is a sector probe that performs sector scans, a convex probe that performs offset sector scans, and a linear probe that performs linear scans, for example. Alternatively, in the first embodiment, for the three-dimensional scanning of the subject P, a mechanical 4D probe and a 2D array probe may be connected to the apparatus body 100 as the ultrasonic probe 11, for example. The mechanical 4D probe is capable of performing two-dimensional scans by using a plurality of piezoelectric transducer elements arrayed in a single row as in the 1D array probe, and is also capable of performing three-dimensional scans by swinging the piezoelectric transducer elements at a certain angle (swing angle). The 2D array probe is capable of performing three-dimensional scans with a plurality of piezoelectric transducer elements disposed in a matrix, and is also capable of performing two-dimensional scans by focusing the ultrasonic waves and transmitting them.

The input device 12 includes a mouse, a keyboard, buttons, panel switches, a touch command screen, a foot switch, a trackball, a joystick, and others; receives various setting requests from an operator of the ultrasonic diagnostic apparatus; and transfers the received various setting requests to the apparatus body 100.

The monitor 13 displays a graphical user interface (GUI) for the operator of the ultrasonic diagnostic apparatus to input various setting requests by using the input device 12, and displays ultrasonic image data and others generated in the apparatus body 100.

The electrocardiograph 14 acquires electrocardiogram (ECG) of the subject P as a biosignal of the subject P that is ultrasonically scanned. The electrocardiograph 14 transmits the acquired electrocardiogram to the apparatus body 100.

The apparatus body 100 is a device that generates ultrasonic image data based on the reflected wave signal received by the ultrasonic probe 11. The apparatus body 100 illustrated in FIG. 1 is a device capable of generating two-dimensional ultrasonic image data based on two-dimensional reflected wave data received by the ultrasonic probe 11. Furthermore, the apparatus body 100 illustrated in FIG. 1 is a device capable of generating three-dimensional ultrasonic image data based on three-dimensional reflected wave data received by the ultrasonic probe 11. In the following description, the three-dimensional ultrasonic image data may be described as "volume data."

The apparatus body 100 includes, as illustrated in FIG. 1, the transmitting-and-receiving unit 110, a B-mode processor 120, a Doppler processor 130, an image generator 140, an image memory 150, an internal storage unit 160, an image processor 170, and a controller 180.

The transmitting-and-receiving unit 110 includes a pulse generator, a transmission delay unit, a pulsar, and others, and supplies a drive signal to the ultrasonic probe 11. The pulse generator repeatedly generates rate pulses to form ultrasonic waves at a certain rate frequency. The transmission delay unit gives, to each of the rate pulses generated by the pulse generator, a delay time that is necessary for each of the piezoelectric transducer elements to focus the ultrasonic waves generated by the ultrasonic probe 11 in a beam shape and to determine the transmission directivity. The pulsar applies the drive signal (drive pulses) to the ultrasonic probe 11 at the timing based on the rate pulses. That is, the transmission delay unit optionally adjusts the transmission direction of the ultrasonic waves transmitted from the plane of the piezoelectric transducer elements by varying the delay time given to the respective rate pulses.

The transmitting-and-receiving unit 110 has a function capable of instantly changing a transmission frequency, a transmission drive voltage, and others in order to execute a certain scan sequence based on the instructions of the controller 180 which will be described later. The change in the transmission drive voltage in particular is implemented by an oscillator circuit of a linear amplifier type that can instantly switch the value thereof or by a mechanism that electrically switches a plurality of power supply units.

The transmitting-and-receiving unit 110 further includes a pre-amplifier, an analog-to-digital (A/D) converter, a reception delay unit, an adder, and others, and generates reflected wave data by performing a variety of processing on the reflected wave signal received by the ultrasonic probe 11. The pre-amplifier amplifies the reflected wave signal for each channel. The A/D converter performs A/D conversion on the amplified reflected wave signal. The reception delay unit gives a delay time necessary to determine the reception directivity. The adder performs addition processing of the reflected wave signal processed by the reception delay unit and generates the reflected wave data. The addition processing of the adder emphasizes the reflection component of the reflected wave signal from the direction corresponding to the reception directivity, and the reception directivity and the transmission directivity form an overall beam of ultrasonic transmission and reception.

The transmitting-and-receiving unit 110, when the two-dimensional scanning of the subject P is performed, transmits a two-dimensional ultrasonic beam from the ultrasonic probe 11. The transmitting-and-receiving unit 110 then generates two-dimensional reflected wave data from a two-dimensional reflected wave signal received by the ultrasonic probe 11. When the three-dimensional scanning of the subject P is performed, the transmitting-and-receiving unit 110 transmits a three-dimensional ultrasonic beam from the ultrasonic probe 11. The transmitting-and-receiving unit 110 then generates three-dimensional reflected wave data from a three-dimensional reflected wave signal received by the ultrasonic probe 11.

The form of the output signal from the transmitting-and-receiving unit 110 is selectable from various forms such as a case of a signal referred to as a radio frequency (RF) signal in which phase information is included and a case of amplitude information after envelope detection processing.

The B-mode processor 120 receives the reflected wave data from the transmitting-and-receiving unit 110, performs the processing of logarithmic amplification, envelope detection, and others, and generates data in which the signal intensity is expressed by the brightness of luminance (B-mode data).

The Doppler processor 130 performs frequency analysis of velocity information on the reflected wave data received from the transmitting-and-receiving unit 110; extracts blood flow, tissue, and echo components of contrast agent by the Doppler effect; and generates data (Doppler data) in which moving body information such as velocity, dispersion, power, and others has been extracted on multi-points.

The B-mode processor 120 and the Doppler processor 1303 in the first embodiment can perform processing on both two-dimensional reflected wave data and three-dimensional reflected wave data. That is, the B-mode processor 120 generates two-dimensional B-mode data from the two-dimensional reflected wave data and generates three-dimensional B-mode data from the three-dimensional reflected wave data. The Doppler processor 130 generates two-dimensional Doppler data from the two-dimensional reflected wave data and generates three-dimensional Doppler data from the three-dimensional reflected wave data.

The image generator 140 generates ultrasonic image data from the data generated by the B-mode processor 120 and the Doppler processor 130. That is, the image generator 140 generates two-dimensional B-mode image data that represents the intensity of reflected waves in luminance from the two-dimensional B-mode data generated by the B-mode processor 120. The image generator 140 further generates two-dimensional Doppler image data that represents the moving body information from the two-dimensional Doppler data generated by the Doppler processor 130. The two-dimensional Doppler image data is velocity image data, dispersion image data, power image data, or image data of the combination of the foregoing. The image generator 140 is further capable of generating Doppler waveforms in which the velocity information on blood flow and tissue is plotted in time series from the Doppler data generated by the Doppler processor 130.

The image generator 140, in general, converts the rows of scanning line signal of ultrasonic scans into the rows of scanning line signal of a video format typified by television and the like (scan conversion), and generates ultrasonic image data for display. Specifically, the image generator 140 generates the ultrasonic image data for display by performing coordinate conversion according to the scanning form of ultrasonic waves by the ultrasonic probe 11. The image generator 140, as a variety of image processing other than the scan conversion, by using a plurality of image frames after scan conversion, further performs image processing (smoothing processing) to regenerate a mean-value image of luminance and image processing (edge enhancement processing) that uses a differential filter within the images, for example. The image generator 140 further combines character information on various parameters, scales, body marks, and others with the ultrasonic image data.

That is, the B-mode data and the Doppler data are ultrasonic image data before scan conversion processing, and the data that the image generator 140 generates is the ultrasonic image data for display after scan conversion processing. The B-mode data and the Doppler data are also referred to as raw data.

Furthermore, the image generator 140 generates three-dimensional B-mode image data by performing coordinate conversion on the three-dimensional B-mode data generated by the B-mode processor 120. The image generator 140 further generates three-dimensional Doppler image data by performing coordinate conversion on the three-dimensional Doppler data generated by the Doppler processor 130. That is, the image generator 140 makes "three-dimensional B-mode data and three-dimensional Doppler data" into "three-dimensional ultrasonic image data (volume data)."

Moreover, the image generator 140 performs rendering processing on volume data to generate a variety of two-dimensional image data so as to display the volume data on the monitor 13. The rendering processing performed by the image generator 140 includes the processing of generating MPR image data from the volume data by performing multi-planar reconstruction (MPR). Furthermore, the rendering processing performed by the image generator 140 includes the processing of performing "curved MPR" on volume data and the processing of performing "maximum intensity projection" on volume data. The rendering processing performed by the image generator 140 further includes volume rendering (VR) processing.

The image memory 150 is a memory that stores therein the image data for display generated by the image generator 140. The image memory 150 can further store therein the data generated by the B-mode processor 120 and the Doppler processor 130. The B-mode data and the Doppler data stored in the image memory 150 can be called up by the operator after diagnosis, and are made into the ultrasonic image data for display via the image generator 140, for example.

The image generator 140 stores ultrasonic image data and the time of ultrasonic scan performed to generate the ultrasonic image data, in the image memory 150, being associated with the electrocardiogram transmitted from the electrocardiograph 14. The image processor 170 and the controller 180 which will be described later can acquire a cardiac phase at the time when the ultrasonic scan was performed to generate the ultrasonic image data by referring to the data stored in the image memory 150.

The internal storage unit 160 stores therein control programs to perform ultrasonic transmission and reception, image processing, and display processing; and a variety of data such as diagnostic information (for example, patient ID and doctor's findings), diagnosis protocols, and various body marks. The internal storage unit 160 is used also for the storage of the image data stored in the image memory 150 as necessary. The data stored in the internal storage unit 160 can be transferred to an external device via an interface not depicted. The external device includes a high-performance work station for image processing, a personal computer (PC) used by a doctor who performs image diagnosis, a storage medium such as a CD and a DVD, and a printer, for example.

The image processor 170 is installed in the apparatus body 100 to provide motion information on tissue that periodically moves. For example, the image processor 170 calculates the motion information on cardiac wall by acquiring ultrasonic image data of the heart stored in the image memory 150 and performing wall motion tracking (WMT) of the heart by image processing. The image processor 170 then stores the generated motion information in the image memory 150 and the internal storage unit 160. The processing of the image processor 170 to calculate the motion information will be described later.

The controller 180 controls the overall processing of the ultrasonic diagnostic apparatus. Specifically, based on the various setting requests received from the operator via the input device 12, and on various control programs and a variety of data read in from the internal storage unit 160, the controller 180 controls the processing of the transmitting-and-receiving unit 110, the B-mode processor 120, the Doppler processor 130, the image generator 140, and the image processor 170. Furthermore, the controller 180 performs control so that the ultrasonic image data for display stored in the image memory 150 and the internal storage unit 160 is displayed on the monitor 13. The controller 180 further performs control so that the processing result of the image processor 17 is displayed on the monitor 13 and output to the external device.

The processing of the image processor 170 to calculate the motion information in the first embodiment will be described. In the following descriptor, explained is a situation in which the image processor 170 calculates motion information on a cardiac wall by performing the wall motion tracking of the heart. The first embodiment, however, is not limited to this. For example, the image processor 170 is capable of generating the motion information on tissue that periodically moves. The image data to be the subject of processing by the image processor 170 may be a two-dimensional ultrasonic image data group and may be a three-dimensional ultrasonic image data group. As for the technology to perform wall motion tracking of the heart, applicable is a known technology such as the technology disclosed in Japanese Patent Application Laid-open No. 2010-194298, for example.

Specifically, the image processor 170 in the first embodiment includes, as illustrated in FIG. 1, an acquiring unit 171, a setting unit 172, a tracking unit 173, and a motion-information calculating unit 174.

The acquiring unit 171 acquires an ultrasonic image data group including a plurality of pieces of ultrasonic image data for at least one heartbeat. For example, with a sector probe, the operator performs two-dimensional scanning or three-dimensional scanning on a region including the heart of the subject P and takes images of moving image data of two-dimensional or three-dimensional ultrasonic image data in which myocardium are extracted. This moving image data is an ultrasonic image data group collected in B-mode, for example. Consequently, the image generator 140 generates moving image data of the myocardium and stores the generated moving image data in the image memory 150. The operator then defines a section for one heartbeat from an R-wave to a subsequent R-wave in the electrocardiogram as the section of processing target, for example. The first embodiment can be applied ever, when the section of processing target is defined as a section for two heartbeats and as a section for three heartbeats.

For example, the acquiring unit 171 acquires a volume data group from the image memory 150. This volume data group includes ultrasonic volume data of a plurality of frames included in the section for one heartbeat defined by the operator.

The setting unit 172 sets a plurality of composition points at positions corresponding to the contours of tissue in at least one piece of ultrasonic image data included in the ultrasonic image data group. When the motion information on the cardiac wall that periodically moves is provided, the contours of tissue are the contours of endocardium and the contours of epicardium, for example. In the first embodiment, the setting unit 172 sets a plurality of composition points constituting the contours at positions corresponding to the initial contours of the heart according to the information the operator has manually set.

The operator first specifies a certain cardiac phase on the volume data group acquired by the acquiring unit 171. The cardiac phase that is specified here is a certain frame out of the frames included in the section for one heartbeat, and is an end-diastolic phase (the first R-wave phase), for example. When the cardiac phase is specified by the operator, the setting unit 172 causes the image generator 140 to execute MPR processing on the volume data of the heart at the specified cardiac phase, and to display on the monitor 13 an MPR cross-section (reference MPR cross-section) serving as the reference in setting the initial contours. While a situation in which the end-diastolic phase is specified as the cardiac phase has been exemplified, it is not limited to this and it may be an end-systolic phase, for example.

The operator specifies that an apical four-chamber view (A4C) is displayed as the first reference MPR cross-section (MPR1) and an apical two-chamber view (A2C) is displayed as the second reference MPR cross-section (MPR2), for example. The operator then inputs respective initial contours on the displayed apical four-chamber view and the apical two-chamber view. On the MPR cross-sections, displayed are not only the endocardium and the epicardium but also the papillary muscle and the tendinous cord. Thus, the operator specifies the initial contours at the cardiac end-diastolic phase such that the extracted papillary muscle and the tendinous cord are not included while observing the displayed reference MPR cross-sections.

When the initial contours are input on a plurality of reference MPR cross-sections, the setting unit 172 generates three-dimensional initial contours from the received two-dimensional initial contours by a known method. Specifically, the setting unit 172 generates three-dimensional initial contours P_endo from the initial contours of the endocardium specified on the MPR1 and MPR2. The setting unit 172 further generates three-dimensional initial contours P_epi from the initial contours of the epicardium specified on the MPR1 and MPR2.

The setting unit 172 then gives respective addresses to a plurality of composition points constituting the three-dimensional initial contours of the endocardium and the epicardium. This address is a number given to identify each of the composition points, and is defined based on the position of the respective composition points of the endocardium, for example. The address is not limited to numbers and may be identification information that can identify the position of each composition point such as characters and symbols, for example.

The setting unit 172 defines the position of each composition point of the endocardium as P_endo(t,h,d) and defines the position of each composition point of the epicardium as P_epi(t,h,d), for example. The t represents a frame (cardiac phase) that is included in the section for one heartbeat, the h represents an address number in a long axis direction, and the d represents an address number in a circumferential direction. Here, t=0 because the initial cross-section is set by using the first R-wave phase.

Figure 2:
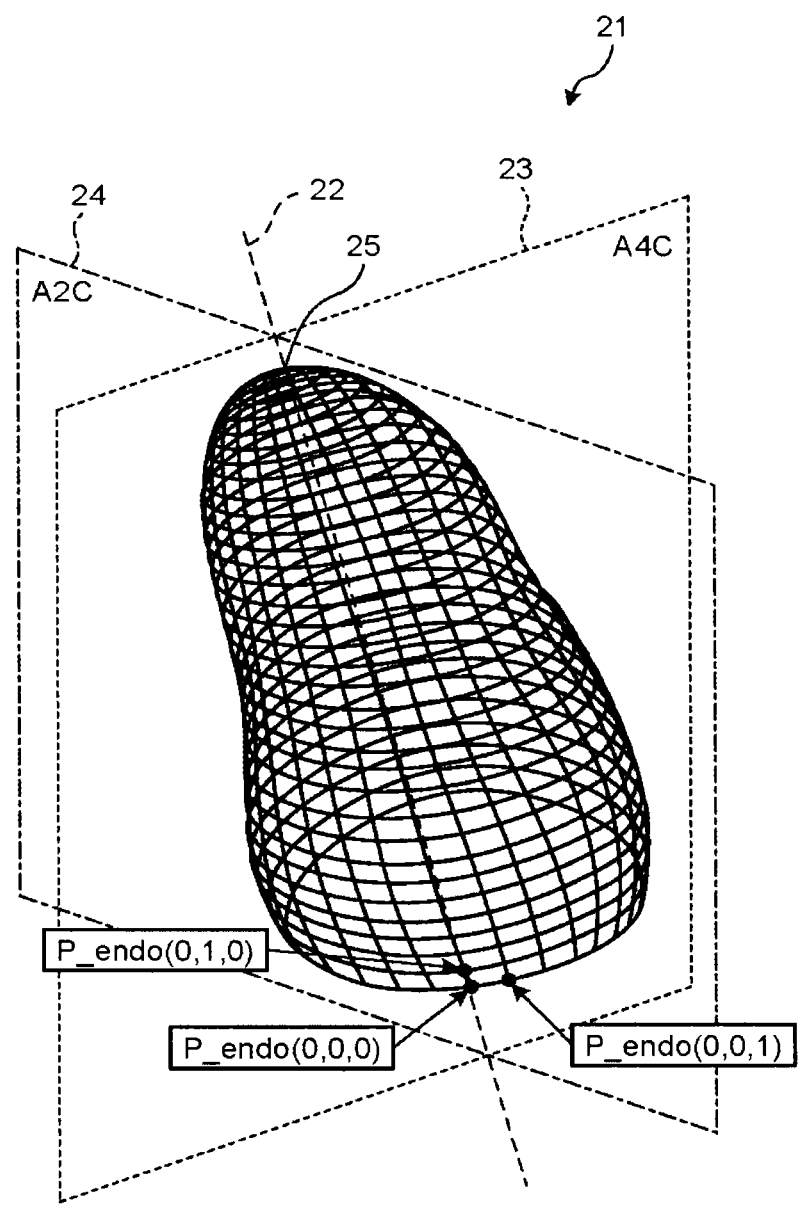
FIG. 2 is a diagram illustrating one example of initial contours set by an operator.

FIG. 2 is a diagram illustrating one example of initial contours set by the operator. In the example illustrated in FIG. 2, a situation of setting initial contours on endocardium contours 21 is illustrated. Each of the composition points illustrated in FIG. 2 is disposed at the point at which the endocardium contours 21 intersect with each cross-section that lies in a long axis direction 22 and each cross-section (short axis cross-section) that is orthogonal to the long axis direction 22. A plane 23 is the MPR1 (A4C) and a plane 24 is the MPR2 (A2C).

As illustrated in FIG. 2, the setting unit 172 defines one of the positions, at which the initial contours and the MPR1 intersect, as a reference position in the circumferential direction and defines the d of the composition point at that position as zero. That is, the position of the composition point located at the reference position is expressed as P_endo(0,h,0). The setting unit 172 then sets the address numbers to the composition points that lie in the circumferential direction from the composition point at the reference position in sequence as d=1, 2, 3, and so on. The setting unit 172 further defines the position of the annular contours farthest from a cardiac apex portion 25 out of the three-dimensional initial contours as the reference position in the long axis direction, and defines the h of the composition point at that position as zero. That is, the position of the composition point located at the reference position is expressed as P_endo(0,0,d). The setting unit 172 then sets the address numbers to the composition points that lie in the cardiac apex direction from the composition point at the reference position in sequence as h=1, 2, 3, and so on. The setting unit 172 sets the reference position in the circumferential direction and the reference position in the long axis direction and gives the addresses, in the same manner, on the contours of the epicardium.

While a situation in which the initial contours are specified by using two reference MPR cross-sections has been exemplified, the first embodiment is not limited to this. For example, the initial contours may be specified by using two or more of reference cross-sections to the setting unit 172. While a situation in which the apical four-chamber view and the apical two-chamber view are used as the reference MPR cross-sections has been exemplified, it is not limited to this. For example, an apical three-chamber view (A3C) may be used as other long axis cross-sections that run through the central axis of cardiac lumen, and short axis cross-sections (such as SAXA, SAXM, and SAXB) that are orthogonal to the long axis cross-section and furthermore a cross-section that is defined by a certain positional relation to the foregoing cross-sections may be used. The processing of displaying a plurality of reference MPR cross-sections is not limited to the above-described manual operation. For example, the reference MPR cross-sections may be displayed automatically by automatic cross-section detection in which any desired cross-section is automatically detected and displayed from volume data. The specifying of the initial contours is not limited to the above-described manual operation. The setting unit 172 may be configured to specify the initial contours automatically or semi-automatically by using dictionary data of the endocardium contour shape and the epicardium contour shape (for example, statistical data of contours set in the past). Furthermore, the specifying of the initial contours may be performed automatically or semi-automatically by using a boundary detection method that detects boundaries in an image.

The tracking unit 173 tracks the positions of a plurality of composition points in a plurality of pieces of ultrasonic image data included in an ultrasonic image data group by performing processing that includes pattern matching by using the ultrasonic image data to which the composition points are set and the other ultrasonic image data.

For example, when a plurality of composition points are set at positions corresponding to the initial contours to the volume data of the frame t=0 included in a volume data group, the tracking unit 173 tracks the positions of the respective composition points at other frames t by the processing including pattern matching. Specifically, the tracking unit 173 repeatedly performs the pattern matching between the volume data of the frame to which the composition points have been set and the volume data of the frame adjacent to that frame. That is, with the respective composition points P_endo(0,h,d) of the endocardium in the volume data at t=0 as the point of origin, the tracking unit 173 tracks the positions of the respective composition points P_endo(t,h,d) in the volume data of respective frames at t=1, 2, 3, and so on. The tracking unit 173 further tracks the positions of the respective composition points P_epi(t,h,d) of the epicardium in the same manner as that of the respective composition points of the endocardium. As a result, the tracking unit 173 obtains coordinate information of the respective composition points constituting the endocardium and the epicardium on the respective frames included in the section for one heartbeat.

The motion-information calculating unit 174 calculates, by using the positions of a plurality of composition points in a plurality of pieces of ultrasonic image data included in each ultrasonic image data group, motion information representing the motion of tissue for the respective pieces of ultrasonic image data.

The motion information calculated by the tracking unit 173 includes parameters such as displacement of each composition point by each frame, and velocity defined by performing time derivative of the displacement, for example. The motion information, however, is not limited to these parameters and may be the parameters that can be calculated by using the coordinate information of a plurality of composition points in the respective frames included in the section for one heartbeat. Specifically, listed can be various parameters such as the strain that is the rate of change in distance between two points, a strain rate defined by performing time derivative of the strain, an area of a local site of an endocardium surface, a change rate of the area from t=0, a volume defined from the composition points of the endocardium and the composition points of the epicardium, and a change rate of the volume. Furthermore, it is possible for the operator to define a certain parameter such as "the time taken for a certain piece of motion information to reach a peak value."

In the following description, a situation in which the motion-information calculating unit 174 calculates "a time-derivative value of the change rate of area at a local site of an endocardium surface" as the motion information will be explained as one example. The motion information calculated is given to the respective composition points used for the calculation. Specifically, the motion information calculated only from the respective composition points of the endocardium is defined as V_endo(t,h,d) and the motion information calculated only from the respective composition points of the epicardium is defined as V_epi(t,h,d). The motion information calculated from the respective composition points of the endocardium and the epicardium is defined as V(t,h,d). The motion-information calculating unit 174 then stores the calculated motion information in the image memory 150 for each volume data group.

Thus, the image processor 170 calculates, on the ultrasonic image data group, the motion information on the endocardium and the epicardium by the processing of the acquiring unit 171, the setting unit 172, the tracking unit 173, and the motion-information calculating unit 174.

As in the foregoing, the overall configuration of the ultrasonic diagnostic apparatus in the first embodiment has been explained. With this configuration, the ultrasonic diagnostic apparatus 1 in the first embodiment is configured to be able to calculate a comparison result accurately when pieces of the motion information calculated on two different ultrasonic image data groups are compared.

For example, in the ultrasonic diagnostic apparatus 1 in the first embodiment, when a stress echo method that evaluates the motor function of tissue by using ultrasonic image data groups collected before and after stress loading is performed, the image processor 170 is to perform the above-described processing on at least two different ultrasonic image data groups.

Specifically, the image processor 170 sets, on each of the volume data group before stress loading on the subject P and the volume data group after stress loading, a plurality of composition points at positions corresponding to the contours of tissue in the volume data at a certain cardiac phase. The image processor 170 then tracks, for each volume data group, the positions of the composition points in a plurality of pieces of ultrasonic image data included in the respective volume data groups by performing processing that includes pattern matching by using the volume data to which the composition points are set and the other volume data. Then, for each volume data group, the image processor 170 calculates, by using the positions of a plurality of composition points in a plurality of pieces of ultrasonic image data included in each ultrasonic image data group, motion information on the tissue for the respective pieces of ultrasonic image data.

Meanwhile, when pieces of the motion information calculated on two different ultrasonic image data groups are compared, the addresses of the respective composition points set on the two different ultrasonic image data groups to be the subject of comparison dc not always correspond to anatomical positions. For example, when a plurality of composition points are set, unless otherwise the anatomical positions of the reference MPR cross-section that receives the setting of initial contours match in the two ultrasonic image data groups, the deviation is to arise between the addresses, which are given to the respective composition points in the two ultrasonic image data groups, and the anatomical positions.

Figure 3A:
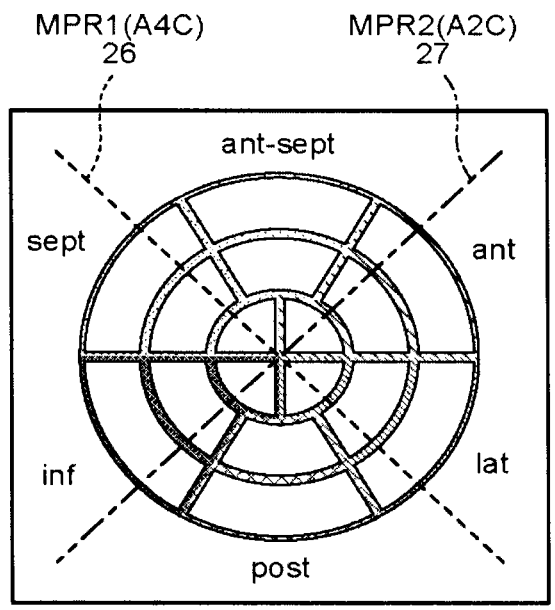
FIGS. 3A and 3B are a diagram illustrating one example of a polar map of a volume data group before stress loading.
Figure 3B:
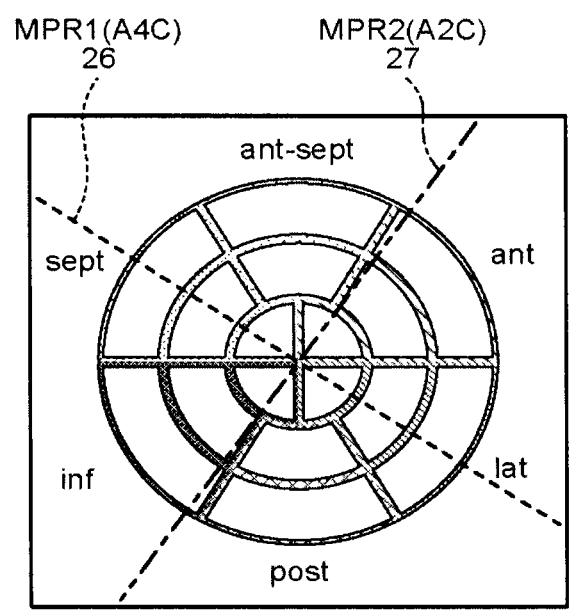

FIG. 3A is a diagram illustrating one example of a polar map of a volume data group before stress loading, and FIG. 3B is a diagram illustrating one example of the polar map of a volume data group after stress loading. The polar map is a display form in which the short axis cross-sections of the endocardium contours 21 from h=0 up to the cardiac apex portion 25 are superposed with the cardiac apex portion 25 as the center. That is, the polar maps illustrated in FIGS. 3A and 3B correspond to a diagram in which the endocardium contours 21 illustrated in FIG. 2 is viewed from the apical side in the long axis direction 22. In FIGS. 3A and 3B, an MPR1 (A4C) position 26 (position of the apical four-chamber view) and an MPR2 (A2C) position 27 (position of the apical two-chamber view) are illustrated.

In the polar maps, as illustrated in FIGS. 3A and 3B, by using the segmented regions recommended by The American Society of Echocardiography and The American Heart Association, the short axis cross-sections of the myocardium of the left ventricle are displayed being divided into six segments of "anteroseptum (ant-sept), anterior wall (ant), lateral wall (lat), posterior wall (post), inferior wall (inf), and septum (sept)."

As illustrated in FIGS. 3A and 3B, between the MPR1 position 26 set in the volume data group before stress loading and the MPR1 position 26 set in the volume data group after stress loading, the positions of anatomical cross-sections may differ. In this case, the deviation arises between the value of the position d in the circumferential direction set with reference to the MPR1 and the anatomical position.

Hence, the ultrasonic diagnostic apparatus 1 in the first embodiment causes the controller 180 to execute the following processing to calculate the comparison result accurately when comparing pieces of the motion information calculated on two different ultrasonic image data groups.

In the following description, in the first embodiment, as a case of comparing pieces of the motion information that has been calculated on two different ultrasonic image data groups, exemplified is a situation in which a stress echo method is performed. The various parameters used in the explanation are defined as follows:

Endocardium composition point before stress loading $P\_endo\_1(t,h,d)$;

Endocardium composition point after stress loading $P\_endo\_2(t,h,d)$;

Epicardium composition point before stress loading $P\_epi\_1(t,h,d)$;

Epicardium composition point after stress loading $P\_epi\_2(t,h,d)$;

Endocardium motion information before stress loading $V\_endo\_1(t,h,d)$;

Endocardium motion information after stress loading $V\_endo\_2(t,h,d)$;

Epicardium motion information before stress loading $V\_epi\_1(t,h,d)$; and

Epicardium motion information after stress loading $V\_epi\_2(t,h,d)$.

The first embodiment is not only applied to a situation in which a stress echo method is performed but also applied widely to the situations of comparing pieces of the motion information calculated from two ultrasonic image data groups, such as before and after medical treatment, immediately after and a few months after medical treatment, and a previous health checkup and the latest health checkup, for example. Furthermore, it may be applied to a situation of comparing the respective pieces of motion information calculated from an ultrasonic image data group of a subject and an ultrasonic image data group of others (for example, a typical ultrasonic image data group of healthy people serving as the reference).

The controller 180 in the first embodiment includes, as illustrated in FIG. 1, a positioning unit 181, a comparison-result calculating unit 182, and an output controller 183.

The positioning unit 181 (identification-information changing unit) performs positioning, based on addresses of a plurality of composition points in first ultrasonic image data included in a first ultrasonic image data group and addresses of a plurality of composition points in second ultrasonic image data of an identical time phase to that of the first ultrasonic image data out of a plurality of pieces of ultrasonic image data included in a second ultrasonic image data group, between the respective pieces of ultrasonic image data included in the first ultrasonic image data group and the respective pieces of ultrasonic image data included in the second ultrasonic image data group.

In other words, the positioning unit 181 changes identification information given to a plurality of points corresponding to the contours of tissue in the first ultrasonic image data included in the first ultrasonic image data group each including a plurality of pieces of ultrasonic image data of different time phases.

For example, the positioning unit 181 acquires two volume data groups to be the subjects of comparison from the image memory 150. The positioning unit 131 then changes the reference position that defines the addresses of the respective composition points set in the respective acquired volume data groups.

Specifically, the positioning unit 181 displays, on the monitor 13, the information indicative of the reference position serving as the reference out of the positions of a plurality of composition points, on the respective volume data included in the two different volume data groups. The positioning unit 181 then performs positioning of the respective volume data, by receiving instructions to change the respective reference positions from the operator and changing the addresses of the composition points in the respective volume data according to the reference positions that have been changed under the instructions. The positioning unit 181 further displays, on the monitor 13, the ultrasonic image data representing the cross-section including the changed reference position each time the reference position is changed under the instructions.

Figure 4:
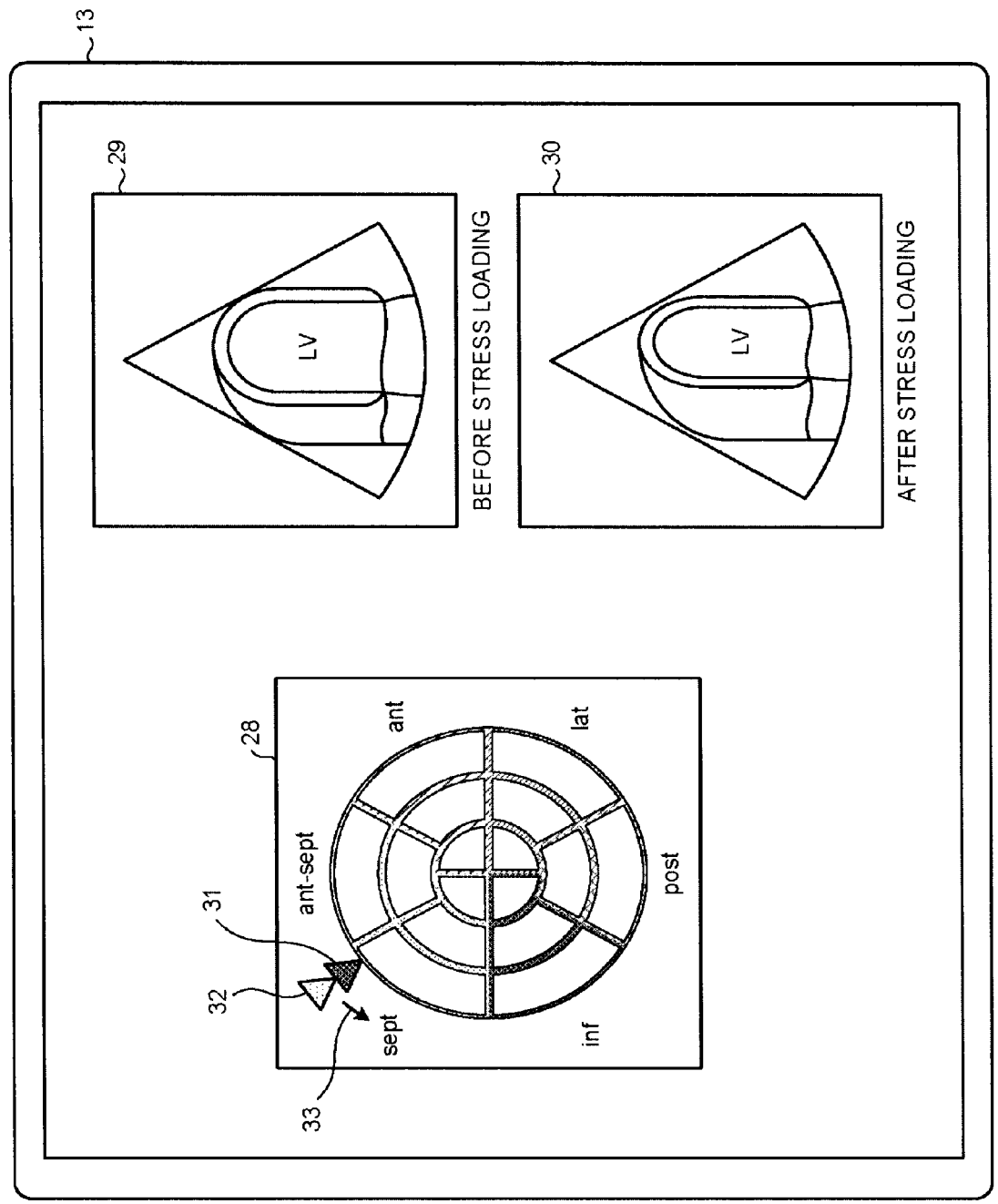
FIG. 4 is a diagram for explaining processing of a positioning unit 181 performed in the first embodiment.

FIG. 4 is a diagram for explaining the processing of the positioning unit 181 performed in the first embodiment. In FIG. 4, illustrated is one example of a display image displayed on the monitor 13 by the processing of the positioning unit 181. In the example illustrated in FIG. 4, the display image displayed on the monitor 13 includes a polar map 28 after stress loading, a display area 29 that displays a tomographic image before stress loading, and a display area 30 that displays a tomographic image after stress loading. The polar map 28 may be of before stress loading. The polar map before stress loading and the polar map after stress loading each may be displayed on the monitor 13.

As illustrated in FIG. 4, the positioning unit 181 displays, on the polar map 28, a marker representing the position of the reference MPR cross-section (d=0). Specifically, the positioning unit 181 causes the image generator 140 to generate and displays, or the monitor 13, a marker 31 representing the position of the endocardium composition point before stress loading P_endo_1(t1,h,0) and a marker 32 representing the position of the endocardium composition point after stress loading P_endo_2(t2,h,0). The positioning unit 181 then causes the image generator 140 to generate and displays, on the display area 29, a tomographic image of long axis cross-section including the position of the marker 31. The positioning unit 181 further causes the image generator 140 to generate and displays, on the display area 30, a tomographic image of long axis cross-section including the position of the marker 32. At this time, the tomographic image on the display area 29 corresponds to the tomographic image of the MPR1 before stress loading, and the tomographic image on the display area 30 corresponds to the tomographic image of the MPR1 after stress loading. Because a left ventricle (LV in FIG. 4) visualized on the display area 30 is visualized narrower than the left ventricle visualized on the display area 29, the operator can determine that the tomographic image on the display area 30 is in an anatomically different position from the tomographic image on the display area 29.

The positioning unit 181 then receives the instructions to change the positions of the marker 31 and the marker 32 from the operator. For example, the positioning unit 181 receives an instruction to move the position of the marker 32 in the direction of an arrow by a drag-and-drop operation of the mouse by the operator.

Figure 5:
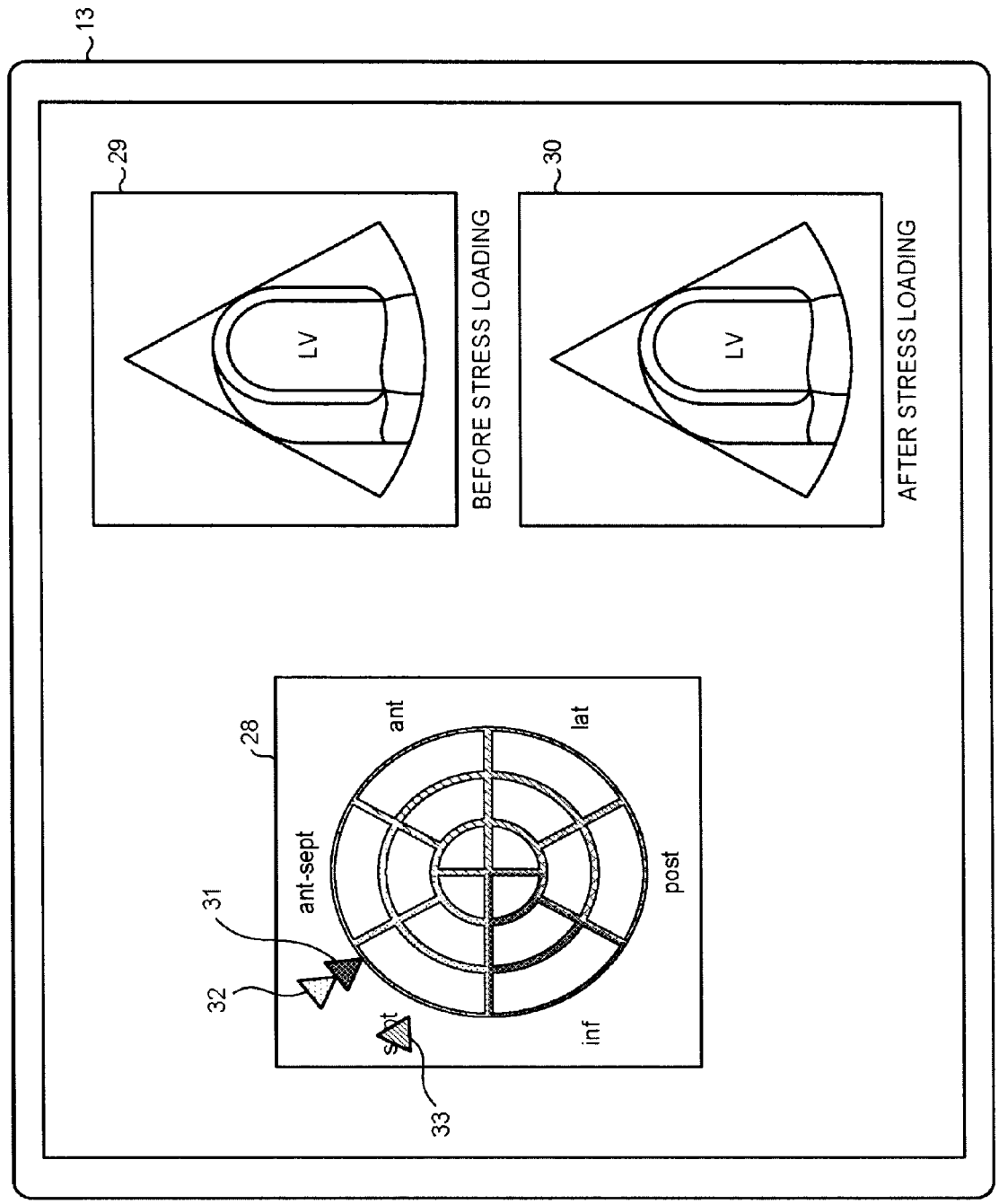
FIG. 5 is a diagram for explaining the processing of the positioning unit 181 performed in the first embodiment.

FIG. 5 is a diagram for explaining the processing of the positioning unit 181 performed in the first embodiment. In FIG. 5, illustrated is one example of the display image when the instruction to move the position of the marker 32 with respect to the display image illustrated in FIG. 4 has been received. In FIG. 5, as long as a marker 33 after moving is displayed, the marker 32 before moving is not necessary to be displayed. However, for the convenience of explanation, a situation of both being displayed is illustrated.

As illustrated in FIG. 5, the positioning unit 181, in response to the instructions received from the operator, moves the position of the marker 32 to the position of the marker 33 and changes the reference position to the position of the marker 33 after moving. That is, the positioning unit 181 rotates, in response to the number of addresses for which the position of the marker 33 has been moved, the reference position in the circumferential direction of the short axis cross-section. Along with this, the positioning unit 181 causes the image generator 140 to generate and displays, on the display area 30, a tomographic image of long axis cross-section including the position of the marker 33 after moving. Consequently, the operator refers to the display area 29 and the display area 30 and changes the position of the marker 33 repeatedly until it is determined that the tomographic image on the display area 29 and the tomographic image on the display area 30 are matched. The operator then, as illustrated in FIG. 5, gives instructions to determine the change in the reference position by using the position of the marker 33 at which it is determined that the tomographic image on the display area 29 and the tomographic image on the display area 30 are matched. While a situation of moving the position of the marker 32 representing the reference position after stress loading has been exemplified, the position of the marker 31 representing the reference position before moving may be moved.

Upon receiving the instructions to determine the change in the reference position, the positioning unit 181 changes the addresses of the composition points according to the changed number of addresses. For example, when the marker 33 after moving has been moved for α addresses in an increasing direction with respect to the marker 32 before moving, the positioning unit 181 moves the address of the respective composition points in the circumferential direction for α addresses by changing the d of the respective composition points to d+α.

For example, when the d is of 100 addresses from 0 to 99 and the marker has been moved for 5 addresses in a decreasing direction, the positioning unit 191 obtains the address of d=50 as d'=50−5=45. When the positioning unit 181 decreases the address of d=0 for 5 addresses, d'=0−5=−5 will result. However, because next to 0 is 99, it comes to 95. As for a computational expression, the positioning unit 181 is to obtain the remainder when (d−α+100) is divided by 100.

While a situation of changing (rotating) the addresses of the respective composition points in the circumferential direction in a certain short axis cross-section has been exemplified, the addresses on the other short axis cross-sections can also be changed by this operation. This is because the positioning unit 181 can obtain the addresses to be changed on the other short axis cross-sections by obtaining, on the other short axis cross-sections, the positions of the reference position that has been changed on this short axis cross-section.

While a situation has been described in which the operator causes the positioning unit 181 to change the addresses of the composition points by giving instructions to determine the change in the reference position after changing the position of the marker, the first embodiment is not limited to this. For example, the operation itself of changing the position of the marker may include the instructions to determine. That is, each time the position of the marker is changed by the operator, the positioning unit 181 may change the addresses of the composition points based on the changed position of the marker.

The comparison-result calculating unit 182 compares the pieces of motion information on ultrasonic image data of an identical time phase included in the first and the second ultrasonic image data groups, and calculates comparison parameters. The comparison parameters are one example of the comparison result.

For example, the comparison-result calculating unit 182 calculates the comparison parameters on the motion information having the identical address on which the positioning has been performed by the positioning unit 181. Specifically, the comparison-result calculating unit 182 calculates the comparison parameters by using the motion information obtained at a certain cardiac phase of at least one or more. The certain cardiac phase referred to is a time phase at which the motion information reaches a peak in early diastole.

However, it is not limited to this and includes a time phase at which the motion information reaches a peak in systole, an end-systolic phase, a time phase at which the motion information reaches a peak in post-diastole, and a time phase at which the motion information reaches a peak in one cardiac cycle.

A situation will be described in which the comparison-result calculating unit 182 calculates comparison parameters by using a peak value of the time derivative value of change rate in local area of an endocardium surface in early diastole at a time phase at which the motion information reaches a peak in the early diastole. The peak value in early diastole is an index representing the dilatation capability of myocardium, and a smaller peak value means a slower dilatation speed of the myocardium. Specifically, when a load is gradually exerted on a subject that is performing a normal dilatation motion before stress loading, the absolute value of the peak value becomes greater than that before stress loading because the pumping function of the heart is increased at a normal myocardium region. In contrast, at a region in which myocardial ischemia and the like is induced and the dilatation capability is deteriorated by the exerted stress load, the absolute value of the peak value is smaller than that before stress loading because the dilatation speed at that region lowers. That is, comparing the peak values in early diastole before and after stress loading enables a normal region of the heart and a deteriorated region of dilatation capability to be distinguished.

The processing of detecting a peak value of motion information in early diastole will be described. For example, the comparison-result calculating unit 182 identifies a time phase at which the volume inside of the endocardium is the smallest, as an end-systolic phase, from the time variation in the respective composition points of the endocardium that are obtained by the tracking unit 173. The comparison-result calculating unit 182 then identifies the period between the identified end-systolic phase and a subsequent R-wave, as a diastolic phase. The comparison-result calculating unit 182 then detects peak values in the diastolic phase, and out of the greatest value and the second greatest value, detects the peak in an earlier phase as a peak value in the diastolic phase. As the peak value in the diastolic phase, the peak in the earlier phase out of the greatest value and the second greatest value is detected, in consideration of a possibility of detecting a peak value that represents the motion of a left ventricular wall caused by left atrial contraction in post-diastole. As for the end-systolic phase, the phase at the end of T-wave detected from the ECG signal may be defined as end-systole. This processing may be performed by the motion-information calculating unit 174.

For example, the comparison-result calculating unit 182 calculates the comparison parameters by using at least one of the following Expression (1) to Expression (3). Expression (1) represents a ratio of the peak after stress loading with respect to that before stress loading, Expression (2) represents a difference between the peak before stress loading and that after stress loading, and Expression (3) represents a change rate of the peak after stress loading with respect to that before stress loading.

$$V\_endo\_2\_max(h,d)/V\_endo\_1\_max(h,d) \quad (1)$$

$$V\_endo\_2\_max(h,d)-V\_endo\_1\_max(h,d) \quad (2)$$

$$\{V\_endo\_2\_max(h,d)-V\_endo\_1\_max(h,d)\}/V\_endo\_1\_max(h,d) \quad (3)$$

In Expression (1) to Expression (3), the term of V_endo_1_max(h,d) represents a peak value in early diastole before stress loading and the term of V_endo_2_max(h,d) represents a peak value in early diastole after stress loading.

For example, the comparison-result calculating unit 182 automatically calculates the comparison parameters by any of the expressions specified in advance out of Expression (1) to Expression (3). Alternatively, the comparison-result calculating unit 182 receives instructions to specify at least one of Expression (1) to Expression (3) from the operator each time the comparison parameters are calculated, and calculates only the comparison parameters by the specified expressions, for example.

The comparison-result calculating unit 182 may calculate the above-described comparison parameters after averaging both pieces of motion information V_endo_1_max and V_endo_2_max(h,d) in a spatial direction, for example. The comparison-result calculating unit 182 calculates the comparison parameters after performing the averaging processing on the respective pieces of motion information in the circumferential direction, for example. This is because performing the averaging processing in the direction in which anatomical positional deviation is likely to occur can reduce the influence of positional deviation in comparison parameters.

The peak value of motion information in early diastole is detectable by not only the foregoing method but also a manual method. For example, as a section desirable to detect peak values, the operator specifies the start and end phases of the section on the ECG displayed on the screen. The period between the vertex of R-wave and the end of T-wave is equivalent to a systolic phase of the cardiac ventricle and that between the end of T-wave and the subsequent vertex of R-wave is equivalent to a diastolic phase. The left atrial contraction occurs at P-wave. Consequently, the start phase of the section desirable to detect peak values is specified near the end of T-wave, and the end phase is specified at any phase up to P-wave from near the end of T-wave. Consequently, the peak values in early diastole can be detected.

The output controller 183 outputs the comparison parameters. For example, the output controller 193 defines colors corresponding to the magnitude of the comparison parameters, and causes the image generator 140 to generate a color image so as to display the comparison parameters in color by using the coordinate information on the respective composition points and information indicative of the colors assigned to those composition points. The output controller 183 subsequently displays, on the monitor 13, the generated color image in a superimposed manner on a volume image (plastic bag, rendering image), an MPR image, a polar map, and the like, for example.

For example, when the comparison parameters are calculated by using the foregoing Expression (3), the output controller 183 expresses the sign "+" of the change rate in a warm color (for example, red), expresses the sign "−" in a cool color (for example, blue), and expresses the magnitude of the change rate in hue (or may be in luminance). Consequently, as a stress load is gradually exerted on a patient who has normal wall motion before stress loading, the pumping function of the heart increases at normal myocardium, and thus the comparison parameter comes to zero or greater and is expressed in the warm color. In contrast, when myocardial ischemia is induced and a deteriorated region in wall motion appears, the comparison parameter at that region turns into a negative value and is displayed in the cool color. Consequently, the normal myocardium and the deteriorated region in wall motion can be easily distinguished.

The output form of the comparison parameters that the output controller 163 outputs is not limited to the above-described color image. For example, the output controller 183 may output the comparison parameters as numerical values to display on the monitor 13, or may generate a graphic chart representing the time variation of the comparison parameters and output it as a graphic chart to display on the monitor 13. The output controller 183 may further store the comparison parameters in various recording media and transmit them to external devices, for example.

Figure 6:
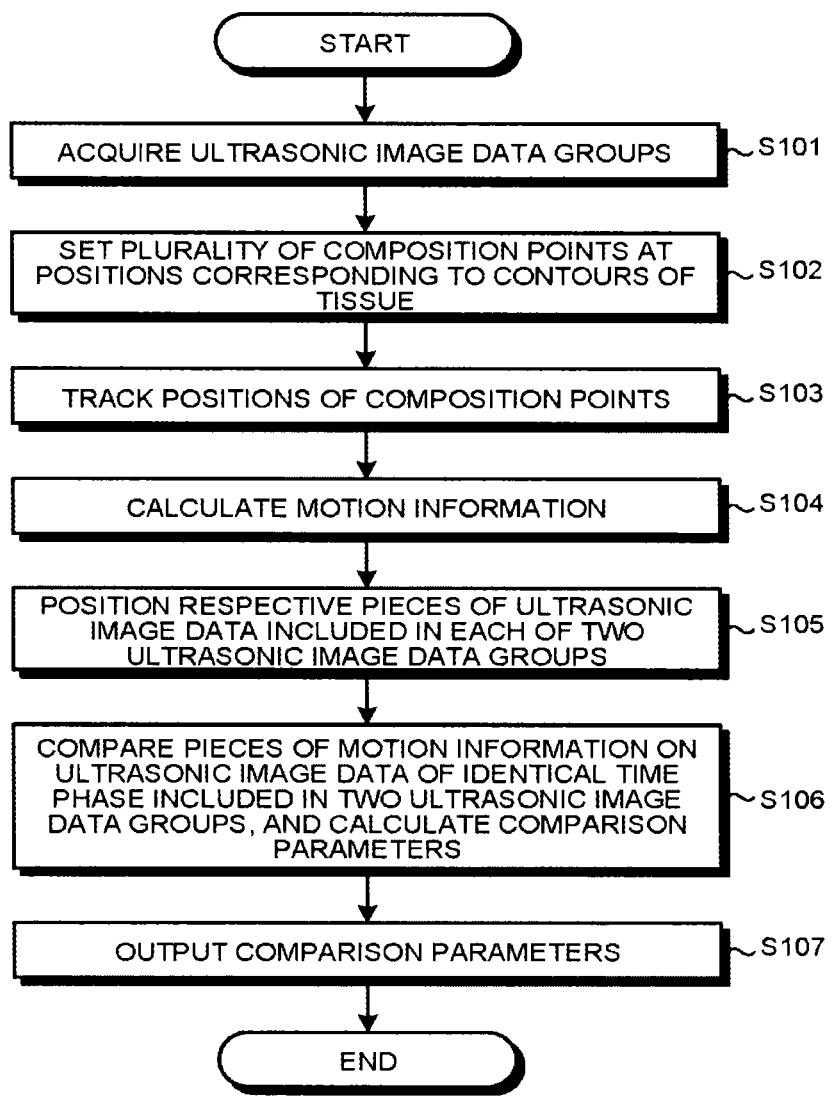
FIG. 6 is a flowchart for explaining processing of the ultrasonic diagnostic apparatus performed in the first embodiment.

FIG. 6 is a flowchart for explaining the processing of the ultrasonic diagnostic apparatus performed in the first embodiment. The processing illustrated in FIG. 6 is started when ultrasonic image data groups to be the subject of processing are specified, for example.

As illustrated in FIG. 6, in the ultrasonic diagnostic apparatus 1 in the first embodiment, the acquiring unit 171 acquires the ultrasonic image data groups to be the subject of processing (Step S01). The setting unit 172 then sets a plurality of composition points at positions corresponding to the contours of tissue in at least one piece of ultrasonic image data included in the ultrasonic image data groups (Step S102).

Subsequently, the tracking unit 173 tracks the positions of a plurality of composition points in a plurality of pieces of ultrasonic image data included in the ultrasonic image data groups, by performing processing that includes pattern matching by using the ultrasonic image data on which the composition points are set and the other ultrasonic image data (Step S103). The motion-information calculating unit 174 then calculates motion information representing the motion of tissue for the respective pieces of ultrasonic image data, by using the positions of the composition points in the respective pieces of ultrasonic image data included in each ultrasonic image data group (Step 3104).

The positioning unit 181 subsequently performs positioning of the respective pieces of ultrasonic image data included in each of the two different ultrasonic image data groups (Step S105). For example, the positioning unit 181 displays, on the monitor 13, the information indicative of a reference position serving as the reference out of the positions of a plurality of composition points, on respective pieces of volume data included in each of the two different volume data groups. The positioning unit 181 then receives instructions to change the respective reference positions from the operator and performs positioning of the respective volume data by changing the addresses of the composition points in the respective volume data according to the reference positions that have been changed under the instructions. The positioning unit 181 further displays, on the monitor 13, the ultrasonic image data representing the cross-section including the changed reference position each time the reference position is changed under the instructions.

The comparison-result calculating unit 182 compares pieces of the motion information on the ultrasonic image data of an identical time phase included in the two ultrasonic image data groups, and calculates comparison parameters (Step S106). The output controller 183 then outputs the calculated comparison parameters (Step S107) and ends the processing.

The above-described processing is one example, and it does not necessarily need to be performed in the foregoing order. For example, the respective pieces of processing of Step S101 to Step S107 illustrated in FIG. 6 need not be performed as a series of processing as illustrated. Specifically, the respective pieces of processing at Step S101 to Step 3104, which constitute the processing to calculate the motion information on the ultrasonic image data groups performed by the image processor 170, and the respective pieces of processing at Step S105 and Step S106, which constitute the processing to perform positioning and comparison on the two different ultrasonic image data groups by the controller 180, may be performed at different timing from each other.

Furthermore, the processing at Step S106 to calculate the comparison parameters by the comparison-result calculating unit 182 does not necessarily need to be performed after the processing at Step S105. Specifically, before the positioning is performed by the positioning unit 181, the comparison parameters may be calculated by comparing pieces of the motion information on the ultrasonic image data of an identical time phase in the two different ultrasonic image data groups. When the positioning unit 181 performs the positioning afterward, the comparison-result calculating unit 182 may calculate the comparison parameters again on the two ultrasonic image data groups on which the positioning has been performed. That is, the comparison-result calculating unit 182 may, each time the positioning is performed by the positioning unit 181, calculate the comparison parameters on the two ultrasonic image data groups on which the positioning has been performed.

That is, in the ultrasonic diagnostic apparatus 1, the positioning unit 181 changes the identification information given to a plurality of points corresponding to the contours of tissue in the first ultrasonic image data included in the first ultrasonic image data group each including a plurality of pieces of ultrasonic image data of different time phases. The comparison-result calculating unit 182 then associates the identification information on the points in the first ultrasonic image data after the change with the identification information given to a plurality of points corresponding to the contours of tissue in the second ultrasonic image data that corresponds to the time phase of the first ultrasonic image data out of the second ultrasonic image data group including a plurality of pieces of ultrasonic image data of different time phases, compares pieces of the motion information representing the motion of the tissue in the respective pieces of ultrasonic image data included in the first ultrasonic image data group and the second ultrasonic image data group between corresponding time phases based on the association, and calculates the comparison result. The output controller 183 then outputs the comparison result. Consequently, on a certain ultrasonic image data group, the operator can change the addresses so that any desired tomographic image is at the reference position.

As in the foregoing, the ultrasonic diagnostic apparatus 1 in the first embodiment performs, based on the addresses of a plurality of points set at positions corresponding to the contours of tissue in the first ultrasonic image data included in the first ultrasonic image data group and the addresses of a plurality of points in second ultrasonic image data of an identical time phase to that of the first ultrasonic image data out of a plurality of pieces of ultrasonic image data included in the second ultrasonic image data group, positioning between each piece of ultrasonic image data included in the first ultrasonic image data group and each piece of ultrasonic image data included in the second ultrasonic image data group, on the first and the second ultrasonic image data groups each including a plurality of pieces of ultrasonic image data for at least one heartbeat. The ultrasonic diagnostic apparatus 1 then compares pieces of the motion information that represents the motion of the tissue on the ultrasonic image data of the identical time phase included in the first and the second ultrasonic image data groups after the positioning is performed, and calculates comparison result. Consequently, the ultrasonic diagnostic apparatus 1 in the first embodiment can calculate the comparison result more accurately.

For example, when pieces of the motion information calculated on two different ultrasonic image data groups are compared, the addresses of the respective composition points set on the two different ultrasonic image data groups to be the subject of comparison do not always correspond to each other. Thus, even if the comparison parameters are calculated by using these two ultrasonic image data groups as they are, it has been difficult to calculate the comparison parameters accurately.

In contrast, the ultrasonic diagnostic apparatus 1 in the first embodiment performs positioning between the addresses of a plurality of composition points in the first ultrasonic image data included in the first ultrasonic image data group and the addresses of a plurality of composition points in the second ultrasonic image data of an identical time phase to that of the first ultrasonic image data out of a plurality of pieces of ultrasonic image data included in the second ultrasonic image data group. The ultrasonic diagnostic apparatus 1 then calculates the comparison parameters on the two ultrasonic image data groups on which the positioning has been performed. Consequently, the ultrasonic diagnostic apparatus 1 can calculate the comparison result more accurately when comparing pieces of the motion information calculated on two different ultrasonic image data groups.

Furthermore, the ultrasonic diagnostic apparatus 1 in the first embodiment displays, on the monitor 13, markers indicative of the reference position serving as the reference out of the positions of a plurality of composition points, on the respective pieces of ultrasonic image data included in the two different ultrasonic image data groups, for example. The ultrasonic diagnostic apparatus 1 then receives the instructions to change the respective reference positions from the operator by the displayed markers and performs positioning of the respective pieces of ultrasonic image data by changing the addresses of the composition points in the respective pieces of ultrasonic image data according to the reference positions that have been changed under the instructions. Consequently, the operator can perform the positioning of the respective pieces of ultrasonic image data groups by simple operation.

The ultrasonic diagnostic apparatus 1 in the first embodiment further displays, on the monitor 13, the ultrasonic image data that represents the cross-section including the changed reference position each time the reference position is changed under the instructions of the operator, for example. Consequently, the operator can change the reference positions on the two ultrasonic image data groups to be the subject of processing while checking the tomographic image of the reference position, and thus can easily specify the position at which the tomographic images of the reference positions match with each other.

Second Embodiment

In the first embodiment, exemplified has been a situation in which the ultrasonic diagnostic apparatus 1 calculates the comparison parameters from the motion information on the frames of an identical time phase included in two different ultrasonic image data groups. In a second embodiment, a situation in which the ultrasonic diagnostic apparatus 1 calculates time-series comparison parameters extending over a plurality of frames will be described.

Figure 7:
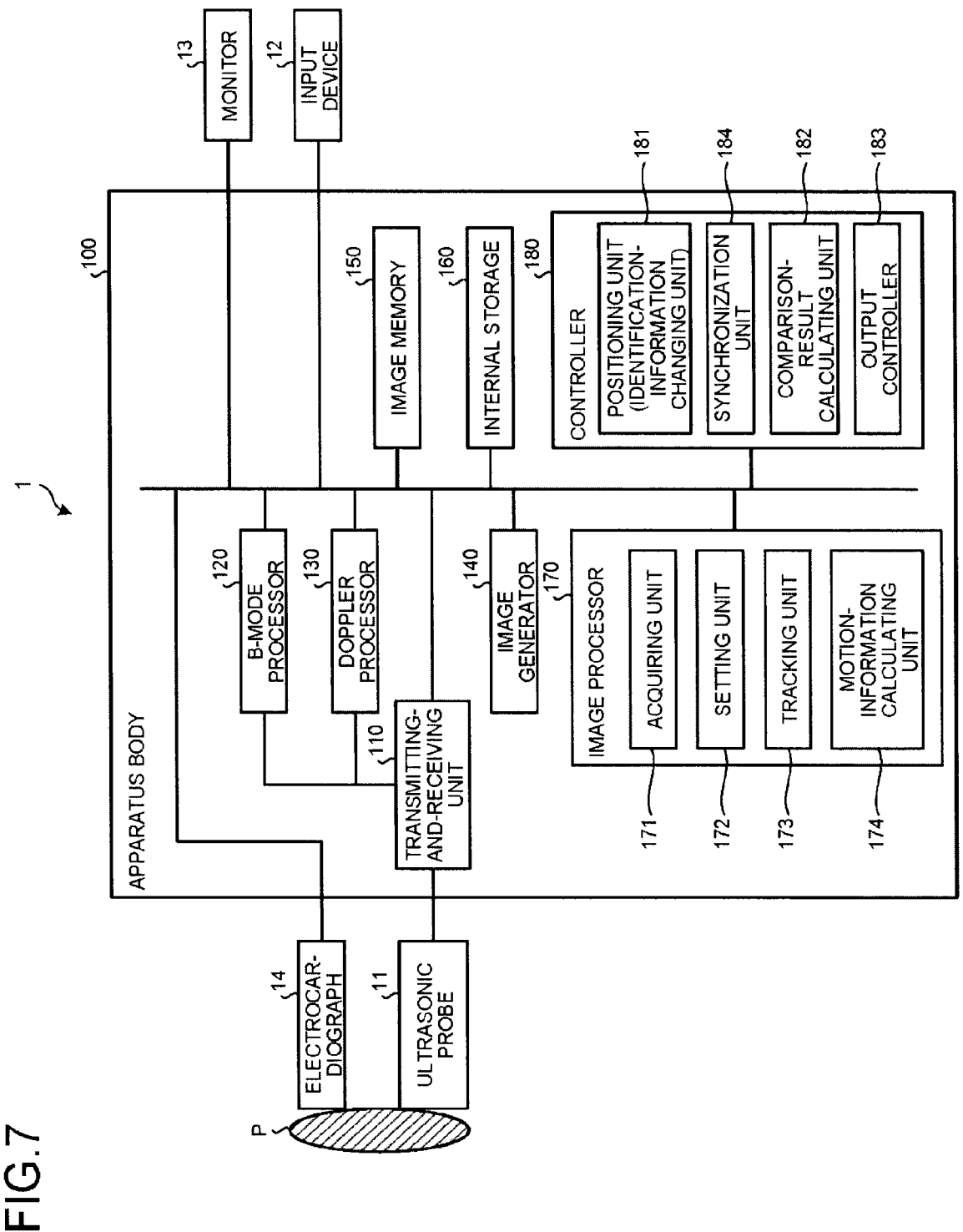
FIG. 7 is a block diagram illustrating an example of the configuration of an ultrasonic diagnostic apparatus according to a second embodiment.

FIG. 7 is a block diagram illustrating an example of the configuration of an ultrasonic diagnostic apparatus according to the second embodiment. As illustrated in FIG. 7, the ultrasonic diagnostic apparatus 1 in the second embodiment differs in terms of including a synchronization unit 184 as compared with the ultrasonic diagnostic apparatus 1 illustrated in FIG. 1 and a part of the processing performed in the comparison-result calculating unit 182 is different. Thus, in the second embodiment, the points that are different from those in the first embodiment will be described, and the descriptions of the same points will be omitted.

The synchronization unit 184 in the second embodiment synchronizes a certain period that is included in one ultrasonic image data group out of two different ultrasonic image data groups, and a period in the other ultrasonic image data group which corresponds to the certain period.

For example, the synchronization unit 184 performs synchronizing at a certain cardiac phase of at least one or more out of the two different volume data groups after the positioning is performed by the positioning unit 181. The certain cardiac phase referred to is a certain section and corresponds to a period such as a systolic phase, a diastolic phase, and one cardiac cycle. The synchronization unit 184 enables the motion information to be compared between corresponding cardiac phases even when the motion information on the frames of perfectly matching cardiac phases is not always present. For example, when pieces of the motion information on the frame at a cardiac phase of 30% of diastole are compared, the ultrasonic image data group of that frame is not always present. In this case, the synchronization unit 184 enables, by interpolating the frame of 30% of diastole by the following synchronization processing, the comparison at the cardiac phase of 30% of diastole to be performed.

Figure 8:
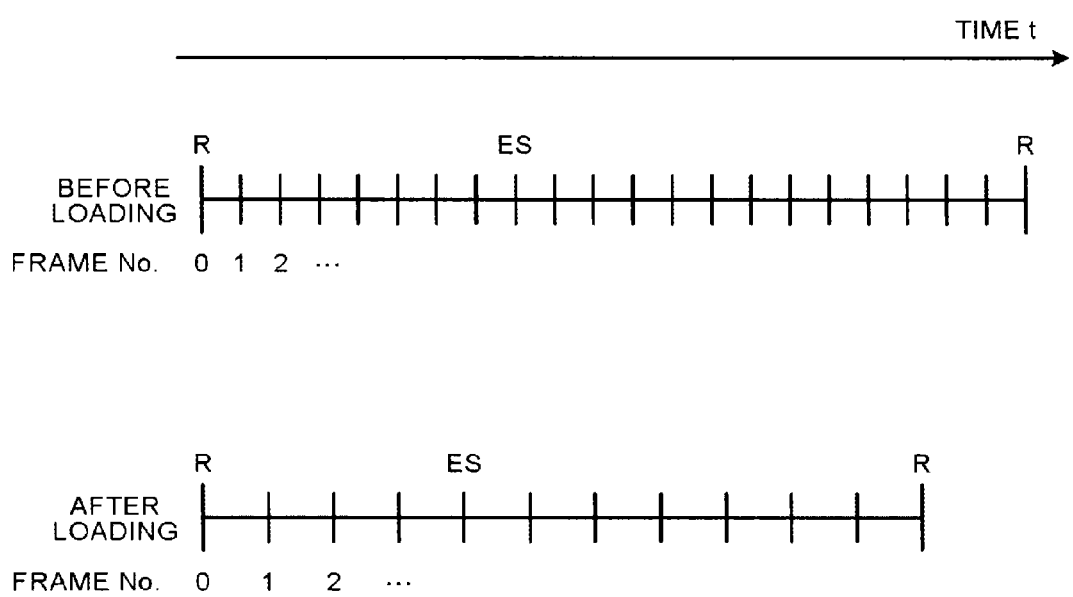
FIG. 8 is a diagram for explaining processing of a synchronization unit 184 performed in the second embodiment.
Figure 9:
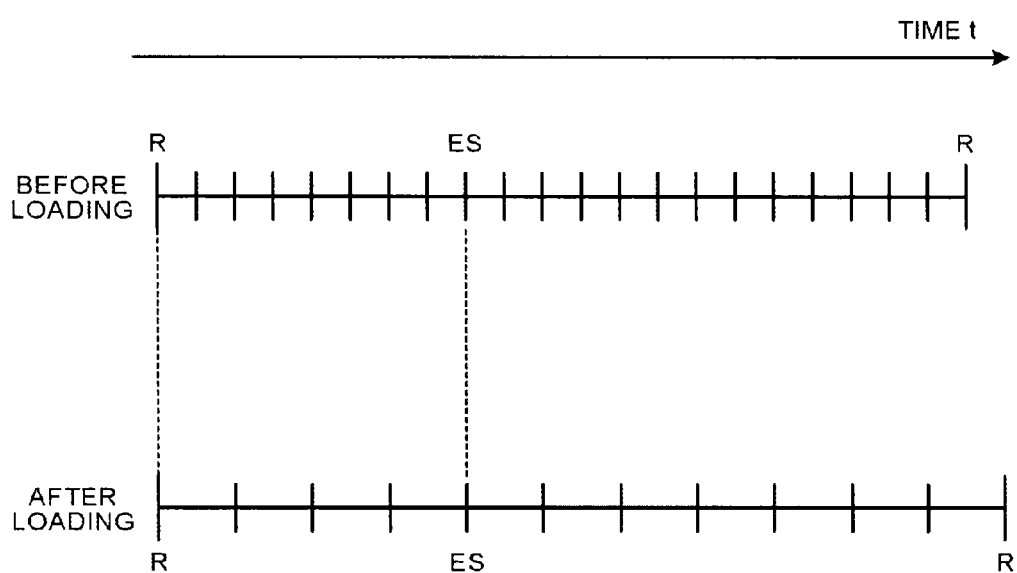
FIG. 9 is a diagram for explaining the processing of the synchronization unit 184 performed in the second embodiment.
Figure 10:
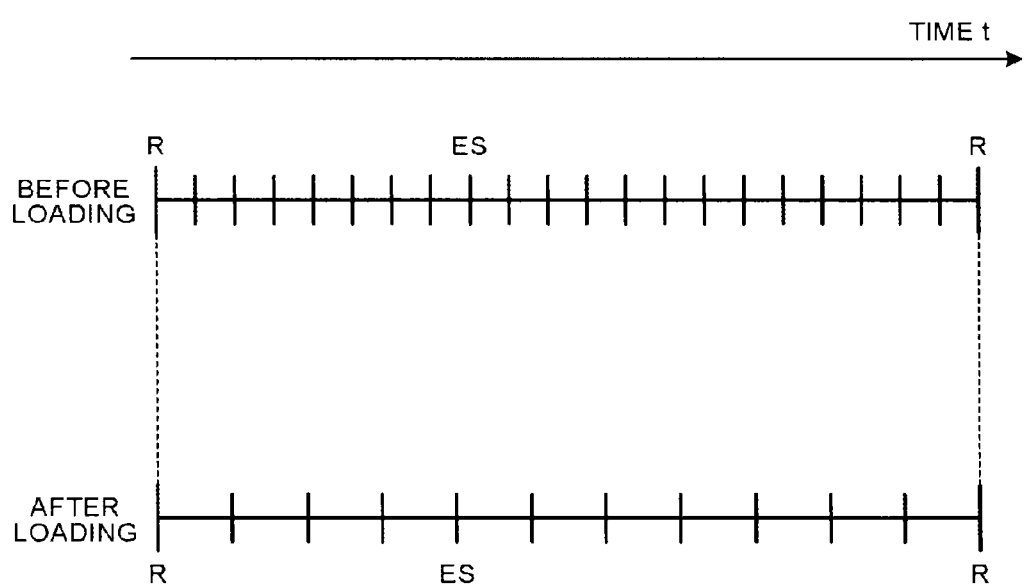
FIG. 10 is a diagram for explaining the processing of the synchronization unit 184 performed in the second embodiment.
Figure 11:
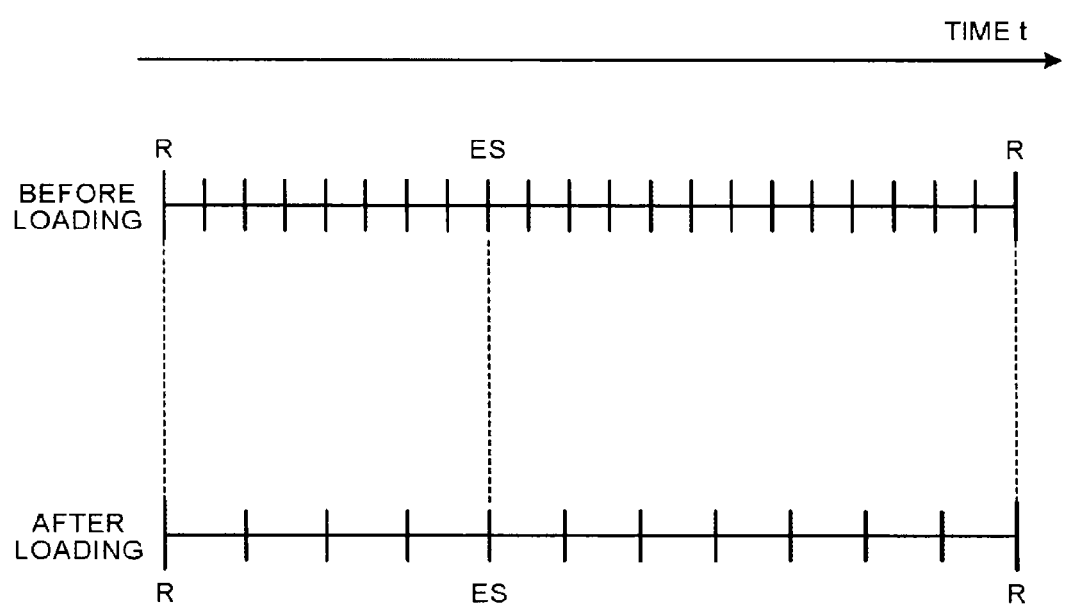
FIG. 11 is a diagram for explaining the processing of the synchronization unit 184 performed in the second embodiment.

FIGS. 8 to 11 are diagrams for explaining the processing of the synchronization unit 184 performed in the second embodiment. In FIG. 8, the frame rate of a volume data group before stress loading and the frame rate of a volume data group after stress loading are illustrated. In FIG. 9, illustrated is a situation in which the two volume data groups illustrated in FIG. 8 are synchronized in an R-ES section. In FIG. 10, illustrated is a situation in which the two volume data groups illustrated in FIG. 8 are synchronized in an R-R section. In FIG. 11, illustrated is a situation in which the two volume data groups illustrated in FIG. 8 are synchronized in an R-ES section and an ES-R section. The R-ES section represents a section from an R-wave up to a subsequent end systole (ES) in electrocardiogram. The R-R section represents a section from an R-wave up to a subsequent R-wave. The ES-R section represents a section from end systole up to a subsequent R-wave.

As illustrated in FIG. 8, on two different ultrasonic image data groups, the frames of an identical time phase extending over a plurality of frames at the same time are not always present. For example, when the heart rate of the subject P has changed between before stress loading and after stress loading, and when the frame rates to collect the ultrasonic image data groups are different, the frames of the identical time phase extending over a plurality of frames at the same time are not always present. Specifically, in the example illustrated in FIG. 8, on two volume data groups, even when the time of the first R-waves in one cardiac cycle is matched, the frames that match extending over a plurality of frames at the same time are not present thereafter. Hence, as illustrated in FIGS. 9 to 11, the synchronization unit 184 in the second embodiment synchronizes two different ultrasonic image data groups in a certain section out of one cardiac cycle.

As illustrated in FIG. 9, the synchronization unit 184 synchronizes, in an R-ES section out of one cardiac cycle, the frame rate after stress loading with the frame rate before stress loading, for example. Thus, with respect to the respective frames before stress loading, if the frames of an identical time phase are present at the same time in the volume data group after stress loading, the comparison can be performed by the comparison-result calculating unit 182. Furthermore, if the frames of the identical time phase are not present at the same time in the volume data group after stress loading, the synchronization unit 184 associates the frame closest to the frame before stress loading or interpolates a frame corresponding to the frame before stress loading. When a frame is interpolated, the synchronization unit 184 calculates an average value or a weighted-average value of the motion information on the frames before and after the time to interpolate, and uses it as the interpolation frame, for example.

Furthermore, as illustrated in FIG. 10, the synchronization unit 184 may synchronize, in an R-R section out of one cardiac cycle, the frame rate after stress loading with the frame rate before stress loading, for example. As illustrated in FIG. 11, the synchronization unit 184 synchronizes, in both the R-ES section and the ES-R section out of one cardiac cycle, the frame rate after stress loading with the frame rate before stress loading, for example. In the cases illustrated in FIGS. 10 and 11 also, if the frames of an identical time phase are not present at the same time in the volume data group after stress loading, as has been described with reference to FIG. 9, the synchronization unit 184 may associate the frame closest to the frame before stress loading or interpolate a frame corresponding to the frame before stress loading.

As in the foregoing, the synchronization unit 184 synchronizes at a certain cardiac phase such as the R-ES section, the R-R section, and the ES-R section, out of two different volume data groups. The synchronization unit 184 then outputs, to the comparison-result calculating unit 182, the two volume data groups on which the synchronization has been performed.

The comparison-result calculating unit 182 in the second embodiment compares pieces of the motion information on the ultrasonic image data of the same period included in the two different ultrasonic image data groups after the synchronization is performed by the synchronization unit 184, and calculates the comparison parameters.

For example, the comparison-result calculating unit 182 calculates the time-series comparison parameters extending over a plurality of frames included in a certain cardiac phase that has been synchronized by the synchronization unit 184. Specifically, the comparison-result calculating unit 182 calculates the comparison parameters by using at least one of the following Expression (4) to Expression (6).

$$V\_endo\_2(t2,h,d)/V\_endo\_(t1,h,d) \quad (4)$$

$$V\_endo\_2(t2,h,d)-V\_endo\_1(t1,h,d) \quad (5)$$

$$\{V\_endo\_2(t2,h,d)-V\_endo\_1(t1,h,d)\}/V\_endo\_1(t1,h,d) \quad (6)$$

The t2 corresponds to a time phase that has been synchronized with the t1 by the synchronization unit 184 out of the time phase of the V_endo_2. The comparison-result calculating unit 182 selects at least one of the above-described Expression (1) to Expression (3) and calculates the time-series comparison parameters extending over the respective frames included in a certain cardiac phase that has been synchronized by the synchronization unit 184.

As in the foregoing, the ultrasonic diagnostic apparatus 1 in the second embodiment can calculate the time-series comparison parameters by performing the synchronization in a certain cardiac phase after the positioning is performed and calculating the comparison parameters extending over the respective frames included in the certain cardiac phase that has been synchronized.

Third Embodiment

While the first and the second embodiments have been described above, the embodiments may be implemented in various different forms other than those of the foregoing embodiments.

Address

In the above-described embodiments, the numbers given to the respective composition points have been exemplified as addresses, for example. However, the address is not limited to numbers, and may be identification information that can identify the position of the respective composition points such as characters and symbols, for example. That is, the addresses are the identification information given to a plurality of points corresponding to the contours of tissue. In the foregoing embodiments, as has been described with reference to FIG. 2, the addresses are given to the respective composition points according to a certain rule.

Change in Identification Information

In the above-described embodiments, described have been situations in which the ultrasonic diagnostic apparatus 1 performs the positioning of two different ultrasonic image data groups, for example. The embodiments, however, are not limited to this. For example, it may be a situation in which the ultrasonic diagnostic apparatus 1 changes the addresses (identification information) that have already been given to one ultrasonic image data group.

Specifically, in the example illustrated in FIG. 4, described has been the positioning in which the address after stress loading is matched to the address before stress loading by the operator moving the marker 32 in the arrow direction while visually checking (comparing) the respective tomographic images on the display area 29 and the display area 30. The operator, however, does not necessarily need to compare the respective tomographic images on the display area 29 and the display area 30 to be capable of changing the address.

As one example, described is a situation in which the address is changed when the polar map 28 and the display area 30 are displayed on the display area of the monitor 13 in FIG. 4. In this case, the positioning unit 181 receives the instructions to move the position of the marker 32 in the arrow direction from the operator. The positioning unit 181, in response to the instructions received from the operator, moves the position of the marker 32 to the position of the marker 33 and changes the reference position to the position of the marker 33 after moving (see FIG. 5). Along with this, the positioning unit 181 causes the image generator 140 to generate a tomographic image of long axis cross-section including the position of the marker 33 after moving and display it on the display area 30. Consequently, the operator can repeatedly change the position of the marker 33 until it is determined that any desired tomographic image is displayed on the display area 30. Then, upon receiving the instructions to determine the change in the reference position from the operator, the positioning unit 181 changes the addresses of the composition points according to the changed number of addresses. The computational expression used for the change in address is the same as the above-described computational expression, and thus its explanation is omitted.

Positioning of Two-Dimensional Images

In the above-described embodiments, described have been situations in which the positioning is performed on the three-dimensional volume data collected by the ultrasonic probe 11. However, it need not necessarily be three-dimensional volume data. For example, when two different two-dimensional short-axis images are acquired, the positioning may be performed by displaying the markers indicative of the reference positions on the respective short-axis images.

Comparison Between Corresponding Time Phases

In the above-described embodiments, described have been situations of comparing pieces of the motion information on the ultrasonic image data of the identical time phase. However, this does not mean the comparison only between the frames the time phases of which perfectly match. That is, on two different ultrasonic image data groups that are the subjects of comparison, even when the frames of a perfectly matching time phase are not present, it is possible to compare pieces of the motion information between the corresponding time phases. For example, the comparison may be performed between the frames the time phases of which are close to each other and the comparison may be performed by using the frame interpolated by the synchronization processing by the synchronization unit 184.

Application to Internal Organs in Addition to Heart

The internal organs to which the above-described image processing method is applied are not limited to the heart, and may be arterial vessels that repeat the dilatation and contraction in synchronization with the cardiac cycle such as a carotid artery.

Application to Medical Diagnostic Imaging Apparatus

The above-described image processing method may be applied to, in an X-ray diagnostic apparatus, an X-ray CT apparatus, an MRI apparatus, and others, two-dimensional or three-dimensional moving image data of medical image data on which an area of interest can be tracked by template matching processing. That is, the image processing method described in the first and the second embodiments may be performed on a medical diagnostic imaging apparatus in addition to an ultrasonic diagnostic apparatus. The above-described image processing method may further be performed by an image processing apparatus installed independently from a medical diagnostic imaging apparatus.

Others

In the above-described embodiments, the respective constituent elements of the devices and apparatuses illustrated are of functionally conceptual, and do not necessarily need to be configured physically as illustrated. That is, the specific embodiments of distribution or integration of the devices and apparatuses are not limited to those illustrated, and the whole or a part thereof can be configured by being functionally or physically distributed or integrated in any unit according to various types of loads and usage. Furthermore, the whole of or a part of the various processing functions performed in the respective devices and apparatuses can be implemented by a CPU, and a program executed by the CPU, or implemented as hardware by wired logic.

The image processing method described in the foregoing embodiments and modifications can be implemented by executing an image processing program prepared in advance on a computer such as a personal computer and a workstation. This image processing program can be distributed via a network such as the Internet. The image processing program can also be recorded on a computer-readable recording medium such as a hard disk, a flexible disk (FD), a CD-ROM, an MO, and a DVD, and executed by being read out from the recording medium by the computer.

As in the foregoing, in accordance with at least one of the described embodiments, the comparison result can be calculated more accurately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic imaging apparatus, comprising:
circuitry configured to
change identification information given to a plurality of points corresponding to contours of tissue in first medical image data included in a first medical image data group including a plurality of pieces of medical image data of different time phases;
associate the identification information on the respective points in the first medical image data after a change with identification information given to a plurality of points corresponding to the contours of tissue in second medical image data that corresponds to the time phase of the first medical image data out of a second medical image data group including a plurality of pieces of medical image data of different time phases;
synchronize a first period corresponding to at least part of the first medical image data group and a second period corresponding to at least part of the second medical image data group;
compare pieces of motion information representing motion of the tissue in the respective pieces of medical image data included in the at least part of the first medical image data group and the at least part of the second medical image data group between corresponding time phases based on the association after synchronization is performed by the circuitry;
calculate a comparison result; and
output the comparison result.

2. The medical diagnostic imaging apparatus according to claim 1, wherein the circuitry is further configured to compare pieces of the motion information corresponding to identical pieces of identification information out of the respective pieces of motion information included in the first medical image data group and the second medical image data group.

3. The medical diagnostic imaging apparatus according to claim 1, wherein the circuitry is further configured to display, on a display, information indicative of a reference position to be a reference out of positions of the respective points on both the first medical image data and the second medical image data, receive an instruction to change the respective reference positions from an operator, and change the identification information on the respective points in respective pieces of medical image data according to the reference position changed under the instruction, to perform positioning of the respective pieces of medical image data.

4. The medical diagnostic imaging apparatus according to claim 3, wherein the circuitry is further configured to display, on the display, medical image data representing a cross-section including the changed reference position each time the reference position is changed under the instruction when the medical image data is volume data.

5. The medical diagnostic imaging apparatus according to claim 1, wherein the medical diagnostic imaging apparatus is an ultrasonic diagnostic imaging apparatus.

6. The medical diagnostic imaging apparatus according to claim 2, wherein the medical diagnostic imaging apparatus is an ultrasonic diagnostic imaging apparatus.

7. The medical diagnostic imaging apparatus according to claim 3, wherein the medical diagnostic imaging apparatus is an ultrasonic diagnostic imaging apparatus.

8. The medical diagnostic imaging apparatus according to claim 4, wherein the medical diagnostic imaging apparatus is an ultrasonic diagnostic imaging apparatus.

9. The medical diagnostic imaging apparatus according to claim 1, wherein the medical diagnostic imaging apparatus is an ultrasonic diagnostic imaging apparatus.

10. A medical image processing apparatus, comprising:
circuitry configured to
change identification information given to a plurality of points corresponding to contours of tissue in first medical image data included in a first medical image data group including a plurality of pieces of medical image data of different time phases;
associate the identification information on the respective points in the first medical image data after a change and identification information given to a plurality of points corresponding to the contours of tissue in second medical image data that corresponds to the time phase of the first medical image data out of a second medical image data group including a plurality of pieces of medical image data of different time phases;
synchronize a first period corresponding to at least part of the first medical image data group and a second period corresponding to at least part of the second medical image data group;
compare pieces of motion information representing motion of the tissue in the respective pieces of medical image data included in the at least part of the first medical image data group and the at least part of the second medical image data group between corresponding time phases based on the association after synchronization is performed by the circuitry;
calculate a comparison result; and
output the comparison result.

11. A control method, comprising:
changing identification information given to a plurality of points corresponding to contours of tissue in first medical image data included in a first medical image data group including a plurality of pieces of medical image data of different time phases;
associating the identification information on the respective points in the first medical image data after a change and identification information given to a plurality of points corresponding to the contours of tissue in second medical image data that corresponds to the time phase of the first medical image data out of a second medical image data group including a plurality of pieces of medical image data of different time phases;
synchronizing a first period corresponding to at least part of the first medical image data group and a second period corresponding to at least part of the second medical image data group;
comparing pieces of motion information representing motion of the tissue in the respective pieces of medical image data included in the at least part of the first medical image data group and the at least part of the second medical image data group between corresponding time phases based on the association after synchronization is performed by the circuitry;
calculating a comparison result; and
outputting the comparison result.

\* \* \* \* \*